United States Patent [19]

Hubbell et al.

[11] Patent Number: 5,811,629

[45] Date of Patent: Sep. 22, 1998

[54] CRYSTALLIZATION PROCESS FOR PURIFICATION OF PARAXYLENE

[75] Inventors: Douglas S. Hubbell, Sudbury, Mass.; Philippe W. M. Rutten, Delft, Netherlands

[73] Assignee: Raytheon Engineers & Constructors, Inc., Lexington, Mass.

[21] Appl. No.: 710,733

[22] Filed: Sep. 20, 1996

Related U.S. Application Data

[60] Provisional application No. 60/004,139 Sep. 22, 1995.

[51] Int. Cl.⁶ .................................................. C07C 7/14
[52] U.S. Cl. .......................... 585/815; 585/805; 585/813; 585/814
[58] Field of Search ................................. 585/804, 805, 585/812, 813, 814, 815

[56] References Cited

U.S. PATENT DOCUMENTS

| | | | |
|---|---|---|---|
| 3,177,265 | 4/1965 | Lammers | 260/674 |
| 3,467,724 | 9/1969 | Laurich | 260/674 |
| 3,624,172 | 11/1971 | Adams | 260/668 A |
| 4,097,543 | 6/1978 | Haag et al. | 260/672 T |
| 4,117,026 | 9/1978 | Haag et al. | 260/671 R |
| 4,316,368 | 2/1982 | Van Pelt et al. | 62/542 |
| 4,332,599 | 6/1982 | Thijssen et al. | 62/542 |
| 4,433,558 | 2/1984 | Cheng et al. | 62/537 |
| 4,475,355 | 10/1984 | Thijssen et al. | 62/123 |
| 4,491,462 | 1/1985 | Thijssen et al. | 62/542 |
| 4,578,093 | 3/1986 | Cheng et al. | 62/12 |
| 4,588,414 | 5/1986 | Takegami et al. | 23/295 R |
| 4,666,456 | 5/1987 | Thijssen et al. | 23/296 |
| 4,705,624 | 11/1987 | Thijssen | 210/96.1 |
| 4,787,985 | 11/1988 | Roodenrijs | 210/772 |
| 4,952,750 | 8/1990 | Puppel | 585/816 |
| 5,062,862 | 11/1991 | Jansen | 23/295 R |
| 5,284,992 | 2/1994 | Hotier | 585/805 |
| 5,329,060 | 7/1994 | Swift | 585/815 |
| 5,329,061 | 7/1994 | Swift | 585/805 |
| 5,401,476 | 3/1995 | Hotier | 422/222 |
| 5,448,005 | 9/1995 | Eccli et al. | 585/812 |
| 5,498,822 | 3/1996 | Eccli et al. | 585/816 |

FOREIGN PATENT DOCUMENTS 0 340 487  4/1989  European Pat. Off. .

OTHER PUBLICATIONS

Marshall Sittig, "Separation of Individual Alkylbenzenes", pp. 196–229, Aromatic Hydrocarbons Manufacture and Technology.

Aromatic Hydrocarbons; Marshall Sittig; Noyes Data Corporation; 1976.

*Primary Examiner*—Glenn Caldarola
*Assistant Examiner*—Thuan D. Dang
*Attorney, Agent, or Firm*—Lappin & Kusmer LLP

[57] ABSTRACT

Improved process and apparatus for purifying paraxylene from mixed C8-aromatic feedstocks are disclosed in which the use of at least two crystallization stages operated at different temperatures in combination with a final product separator improves purity and recovery while reducing capital and energy costs.

9 Claims, 6 Drawing Sheets

CRYSTALLIZATION PROCESS FOR PURIFICATION OF PARAXYLENE

This application claims the benefit of U.S. Provisional application Ser. No. 60/004,139 filed Sep. 22, 1995.

The present invention relates generally to an improved process for the purification of paraxylene by fractional crystallization.

BACKGROUND OF THE INVENTION

Paraxylene has become increasingly important as the starting material for the production of polyesters, primarily polyethyleneterephthalate (PET), thereby creating a growing market for very high-purity paraxylene. The principal source of paraxylene is petroleum. After reformation of the petroleum fraction with a boiling range of about 65°–175° C., light nonaromatics are separated off by flashing followed by distillation, and then the benzene, toluene, and most of the remaining nonaromatics are distilled in a second distillation column. This distillate stream is subjected to an extraction process in which aromatics are separated from non-aromatic components. Benzene and toluene are recovered as top-products in subsequent distillation steps. A third distillation yields a mixture of the C8-aromatics, particularly ortho-, meta-, paraxylene, and ethylbenzene at the top, and a bottom product that contains heavier aromatics. If orthoxylene is to be recovered as a purified product, part of the orthoxylene is taken off the bottom of the third distillation column and purified in another distillation step.

The C8-aromatic mixture typically is then fed to a unit where paraxylene is separated from its isomers, which are sent to an isomerization unit. Elevated temperatures and the use of a catalyst allow the composition to shift towards equilibrium, and paraxylene is thus produced from its isomers. During the isomerization process, components other than C8-aromatics are unavoidably formed. The lighter byproducts are distilled off and the remaining mixture that consists of C8-aromatics and heavier components is recycled back to the previously-mentioned third distillation column. Because of the close boiling points, the isolation of paraxylene from ethylbenzene by distillation is prohibitively expensive, and the separation of paraxylene from metaxylene by distillation is, for all practical purposes, not possible. Consequently, various crystallization and adsorption processes have been developed and are used commercially for the concentration and isolation of paraxylene from its aromatic isomers and other impurities.

The processes developed and applied on an industrial scale for crystallization of paraxylene, which as a pure compound freezes at +13.3° C., can roughly be divided into two classes with respect to the method-of heat removal: (i) those with direct contact cooling and (ii) processing applying indirect cooling, both of which are generally known in the art.

U.S. Pat. No. 3,177,265, which is incorporated herein by reference, for example, illustrates a conventional indirect-cooled crystallization process for purifying paraxylene. In this process, a fresh feed has about 20 percent paraxylene with the remaining components being primarily the other C-8 hydrocarbon aromatics: orthoxylene, metaxylene, and ethylbenzene. This fresh feed is cooled and partially crystallized down to temperatures in the range of –55° C. to –70° C. in the first of two crystallization stages. The first crystallization is accomplished in a series of vertical scraped-surface jacketed vessel-type crystallizers. The precooled fresh feed is fed to the warmest crystallizer and flows through progressively colder crystallizers. The slurry from the last (coldest) crystallizer is separated by centrifuges into a crystal cake and a filtrate. The crystal cake is melted. The filtrate, or mother liquor, from these first-stage centrifuges is the net filtrate product from the process. Because of eutectic points, this filtrate necessarily still contains at least 7 percent paraxylene. Consequently, the paraxylene recovery for the process is typically less than 65 percent.

The melted cake from the first-stage centrifuges contains about 90 percent paraxylene. This melt is then partially recrystallized at warmer temperatures in a second stage of crystallization. This stage is made up of one or more vessel-type crystallizers in parallel. The partially crystallized stream is centrifuged and washed with recycled paraxylene product to produce paraxylene product with a purity in excess of 99 percent. The second-stage filtrate is recycled back to the first stage.

The present application is directed to processing feeds with paraxylene concentrations in the range of 65 to 98 percent, which includes the feed composition to the second stage of the above described crystallization process. The present invention could thus utilize feed from the first stage of the above described process and can have advantages in efficiency and recovery over the above described crystallizers-in-parallel second stage.

Recent approaches to paraxylene purification have focused on improving the economics of the conventional crystallization processes. For example, U.S. Pat. No. 4,588,414, "Countercurrent Cooling Crystallization and Purification Method for Multicomponent Molten Mixture," which is incorporated herein by reference, describes a process for separating a single pure component from a multi-component mixture using countercurrent crystallization and a final purification step. In this process, a multi-component mixture is fed to a series of vessel-type crystallizers each consisting of an upper portion for clarifying and a lower section with a cooling jacket. The crystallizers are arranged in order of temperature. Except for the coldest crystallizer, the liquid or filtrate from a crystallizer clarifying section is sent to the clarifying section of the next colder crystallizer, while, except for the warmest crystallizer, the crystal slurry from the bottom section of a crystallizer is pumped to the clarifying section of the next warmer crystallizer. From the bottom of the warmest crystallizer, the crystal slurry is pumped to the clarifying section of a purifier. The crystals flow down by gravity through the purifier to a lower heating zone. The crystals are melted in the heating zone and split into a product stream and a reflux stream which is sent back up the purifier to wash the falling crystals. This purifier is sometimes referred to as an unpacked wash column. Before a crystal slurry is transferred to the next crystallizer or to the purifier, liquid may be partially removed by solid-liquid separation with a hydrocyclone, filter, centrifuge or the like. The net filtrate is decanted off the top of the coldest crystallizer.

Relative to the above described conventional indirect-cooling crystallization process, the process described in U.S. Pat. No. 4,588,414 has the advantage that the crystals which form the product are not completely melted and recrystallized. This process saves refrigeration power and reduces the necessary size of the refrigeration equipment. However, some of the heat applied to the purifier melts crystals to produce purifier reflux liquid, which becomes impure and must be recycled and recrystallized. Thus, the refrigeration requirements of this system are still well above minimal levels.

An alternative approach to isolation of paraxylene from a C8-aromatic mixture is by means of molecular sieve adsorption. For feeds with about 20 percent paraxylene, the advantage of this process is a higher paraxylene recovery per pass (over 95 percent) compared with crystallization. Thus, by applying molecular sieve adsorption, more paraxylene can be produced when flowrates for other streams—such as the feedstream to the paraxylene separation unit, the feedstream to the isomerization unit, and the recycle stream to the third distillation column—are kept constant. For this reason, this process is generally economically more attractive than crystallization processes for feeds available from reformation and isomerization, which typically contain about 20 percent paraxylene.

"Parex" is the most widely applied molecular sieve adsorption process, as described in D. P. Thornton, *Hydrocarbon Proc.* 49 (1970) at pp. 151–155, which is incorporated herein by reference. This process is based on the principle of continuous selective adsorption in the liquid phase employing fixed beds of solid adsorbent. The adsorbent is made from zeolite material, and all components are allowed to enter the pore structure. So, the separation technique is not based on shape selectivity but solely on small differences in affinity to the adsorbent. Paraxylene has the strongest affinity to the adsorbent and is thus preferentially adsorbed. The affinity of the desorbent liquid has to lie between those of paraxylene and the other feed components. When the desorbent affinity is too low, it will take a lot of effort to remove the paraxylene from the adsorbent. If the affinity is too high, the paraxylene is not capable of displacing the desorbent from the adsorbent. Furthermore, the volatility of the desorbent should differ sufficiently from that of feed compounds to allow for separation of the paraxylene-desorbent and non-paraxylene-desorbent mixtures by distillation. Paradiethylbenzene has proven to be a suitable desorbent.

The crystallization and molecular sieve adsorption approaches may also be combined in a "hybrid" technology. Thus, U.S. Pat. Nos. 5,284,992 and 5,401,476, which are incorporated herein by reference, teach the concept of concentrating paraxylene up to the range of about 75 to 98 percent, preferably 85 to 98 percent, by molecular sieve adsorption, and then using fractional crystallization to finish the purification to a purity of over 99 percent. This hybrid approach combines certain features of both adsorption and crystallization. Adsorption is used for concentrating the paraxylene because crystallization cannot achieve high recovery from a dilute feed. Crystallization is used for the final purification because an adsorption process is much more expensive when high purities, such as 99 percent, are required with high recoveries. These patents teach that the crystallization unit can be the same as the second stage of conventional crystallization units. Thus, the crystallization unit described by this patent does not improve on the prior crystallization art.

In two similar patents (U.S. Pat. Nos. 5,329,060 and 5,329,061), which are also incorporated herein by reference, the purity of the paraxylene from the adsorption unit in a hybrid arrangement is 65 to 85 percent. In this case, the crystallization unit described is essentially the conventional two-stage crystallization process thereby resulting in the inefficiency of crystallizing the product twice.

A more recently developed technology is Selective Toluene DisProportionation (STDP) (U.S. Pat. Nos. 4,097,543 and 4,117,026). It reacts toluene to form primarily benzene and the C-8 aromatics: paraxylene, metaxylene, orthoxylene, and ethylbenzene. In the reaction product, paraxylene makes up 75 to 95 percent of the C-8 aromatics. These C-8 aromatics can be separated from the other products by commercially viable distillation.

In still another recent development in this field, U.S. Pat. No. 5,448,005, which is incorporated herein by reference, teaches a crystallization process for paraxylene recovery in which a single temperature crystallization production stage is used for producing paraxylene from a feed having an above-equilibrium paraxylene concentration, followed by one or more "scavenger" stages to increase the paraxylene recovery rate. This patent does not, however, suggest the possible utility of a wash column as a final product separator in combination with a controlled crystallization process for optimizing parameters, minimizing energy and capital costs, while obtaining a significantly higher purity paraxylene product. Also, paraxylene recovered in the scavenger stages is partially or totally melted prior to recycling back to the primary crystallization stage, where this heat must be removed using refrigeration. Thus, the energy efficiency of this process could possibly be improved.

As stated earlier, the purification of paraxylene from the approximately 20-percent purity streams typically available in aromatics plants is generally more economically done by adsorption, and not by crystallization, primarily because of the high recovery achieved with adsorption. However, with concentrations above 65 percent paraxylene, crystallization can achieve high recoveries economically with relatively high crystallization temperatures. Thus, the previously described patents on hybrid arrangements of adsorption and crystallization have improved on earlier processes. Paraxylene streams with purities in the range of 65 to 98 percent can come from adsorption units, traditional first-stages of crystallization units, or STDP units. Consequently, there is a need for high-efficiency crystallization processes for purification of feed with at least 65 percent paraxylene, and the present invention has been developed for this specific use.

Other U.S. patents related to paraxylene purification technology include Nos. 3,467,724; 4,433,558; and 4,578,093, all of which are incorporated herein by reference. In addition a chapter of the book *Aromatic Hydrocarbons: Manufacture and Technology* (Noyes Data Corp. 1976) by Marshall Sittig, entitled "Separation of Individual Alkylbenzenes," at pages 196–229, provides a comprehensive discussion of the earlier state of the art in this field and is also incorporated herein by reference.

All of the foregoing prior art processes, however, have various drawbacks ranging from high costs due to excessive energy consumption, complex equipment, and materials handling problems, to an inability to process industrially efficient quantities of product. These and other drawbacks with and limitations of the prior art processes are, at least in part, overcome with the improved crystallization process of this invention.

OBJECTS OF THE INVENTION

Accordingly, a principal object of this invention is to provide a multi-step, relatively high-temperature crystallization process for highly-efficient purification of a relatively concentrated stream of paraxylene.

It is a specific object of this invention to provide improved methods to fractionally crystallize paraxylene from mixed C8-aromatic feeds containing about 65 to 98 percent paraxylene to obtain a highly purified product at or above 99.5 percent purity, preferably above 99.9 percent.

It is also an object of this invention to provide a crystallization process for purification of paraxylene especially adapted to cooperate with certain upstream and downstream processing operations in order to produce industrial quantities of an extremely pure paraxylene product at low cost.

Another object of this invention is to provide a relatively warm (−5° C. to +10° C.) paraxylene slurry to a final product separator (FPS) which, in one preferred embodiment, comprises a packed-bed wash column system as hereinafter described.

Still another object of this invention is to provide a paraxylene purification process designed to crystallize as much product as possible at high temperatures by having two or more crystallizers operating at different temperatures.

Yet another object of this invention is to provide a paraxylene purification process designed to minimize the flow of process material to the lower temperatures of the process.

Another object of this invention is to provide a paraxylene purification process designed to minimize the refrigeration required by limiting or eliminating the need to add heat to the process except for what is required to melt the final product paraxylene, in particular, to provide a paraxylene purification process step prior to the final product separation is carried out in conjunction with substantially eliminating heat input to the process thereby to realize a minimum of net melting of crystals.

Other objects and advantages of the present invention will in part be obvious and will in part appear hereinafter. The invention accordingly comprises, but is not limited to, the processes and related apparatus, involving the several steps and the various components, and the relation and order of one or more such steps and components with respect to each of the others, as exemplified by the following description and the accompanying drawings. Various modifications of and variations on the processes and apparatus as herein described will be apparent to those skilled in the art, and all such modifications and variations are considered within the scope of the invention.

SUMMARY OF THE INVENTION

In general, this invention comprises an efficient multi-stage crystallization process for the final purification of paraxylene from a relatively concentrated feedstream with paraxylene in the concentration range of 65 to 98 percent to obtain a final paraxylene product with a purity at or above 99.5 percent, preferably 99.90 percent or higher. More particularly, all embodiments of the crystallization process in this invention include a final product separator (FPS), a final product separator feed section, and two or more crystallizers operating at different slurry outlet temperatures. The final product separator and other crystal/liquid separators may, for example, be wash columns, centrifuges, or filters. Depending on the feed purity, production rate, and other optimization factors, there may be a third crystallization stage, and the final product separator feed section may be a crystallization stage. Furthermore, all embodiments involve a minimum of net melting of crystals except that necessary for the final conversion of the product from a solid to a liquid. Energy savings are thereby realized, and greater throughput is achieved, as compared with prior art processes, with equal or better purity levels of the resulting paraxylene product.

DETAILED DESCRIPTION OF PREFERRED EMBODIMENTS

Figure 1:
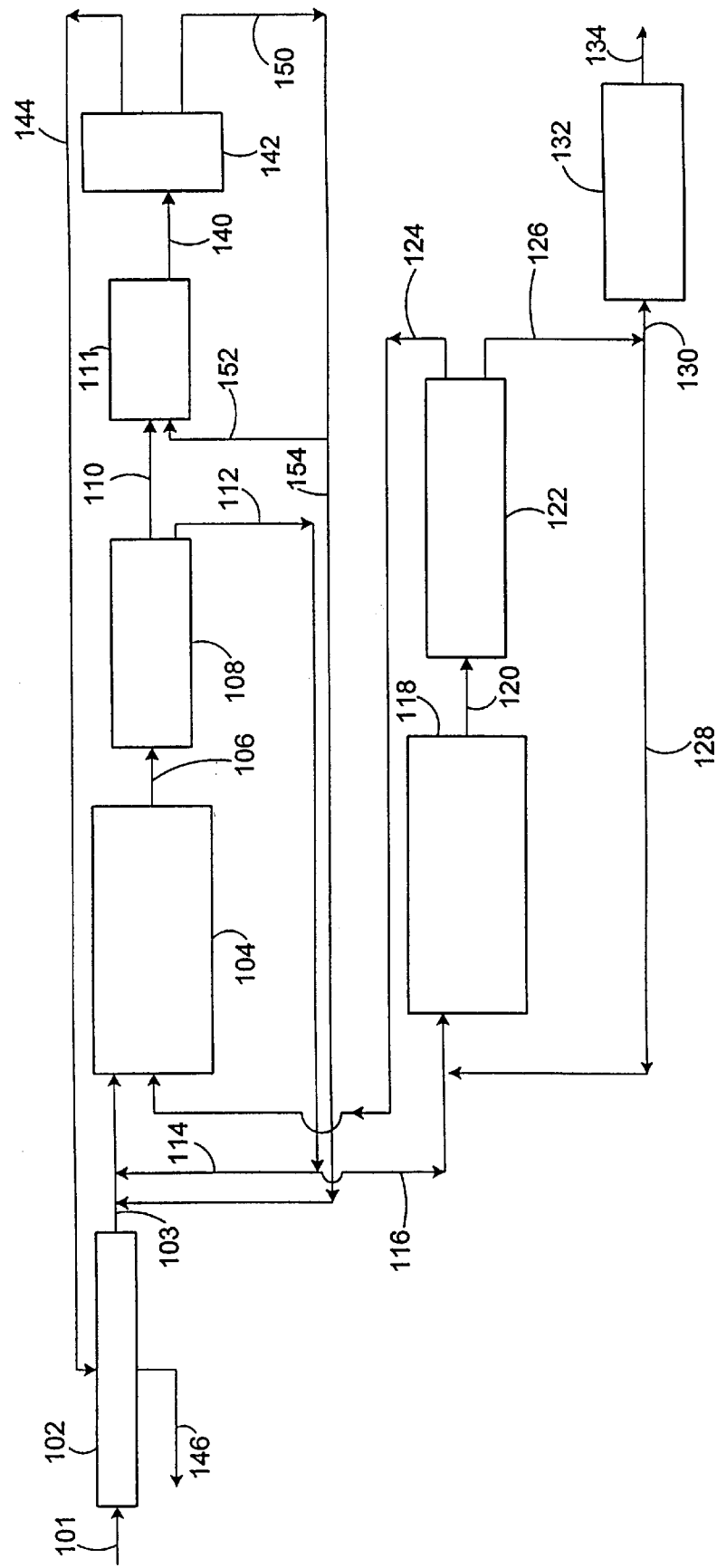
FIG. 1 is a process flow diagram illustrating an embodiment of this invention wherein purified paraxylene is produced by a two-stage process where the final product separator feed section is based on a drum, referred to as a slurry drum, and there is a cold crystallization stage with a cold-stage crystal/liquid separator, which sends crystals to the warm crystallization stage, which is followed by another crystal/liquid separator, which sends its crystals to the slurry drum.

The key to the present invention is the optimization of certain apparatus components and process variables so as to obtain high purity paraxylene product at reasonable cost under a range of production constraints. For example, the best conventional paraxylene purification processes, utilizing centrifuge separations with the product centrifuges employing a wash step, typically achieve a product purity of about 99.7 to 99.8 percent. While it is theoretically possible to achieve 99.9 percent purity with such processes and apparatus, to do so would require an enormous increase in the volume of liquid used in the wash step with concomitant increases in equipment and energy.

In known crystallization processes for purifying paraxylene, there are also certain tradeoffs between product purity and various capital, thermal, and handling costs. The recovery in a crystallization process is determined by how low the temperature is when the net filtrate is separated from the crystals. At least one crystallizer must operate at this crucial temperature. By having other crystallizers operate at higher temperatures, not all of the crystallization is carried out at the minimum (more expensive to operate at) temperature. Higher crystallization temperatures result in faster crystal growth rates which produce larger crystals. The crystals can be very pure, and the key to high product purity is to efficiently separate the product crystals from the accompanying liquid, which has large concentrations of impurities. Large crystals are easier to separate from liquid than small crystals because of the low surface-to-volume ratio and larger spaces between crystals. In the case of wash columns, both packed and unpacked types, larger crystals result in higher equipment capacities. Operating with high crystallization temperatures also minimizes the power required for crystallization refrigeration because lower refrigeration temperatures require lower refrigerant pressures and thus higher refrigeration compressor compression ratios. Thus, increasing the portion of crystallization done at warmer temperature saves capital and operating costs for the refrigeration system.

Furthermore, when operating a crystallization process at multiple temperatures, it is desirable to minimize the flow of process material to the lower temperature operations. Less flow results in less low-temperature cooling requirements, which saves refrigeration power and capital cost. In addition, it is desirable to minimize melting of purified paraxylene crystals until after final crystal separation. Crystal melting caused by heat input followed by recrystallization results in higher refrigeration capacity and power consumption and increased crystallizer surface area. The several embodiments of this invention described herein optimize a number of these process parameters in coordinated, interrelated ways to achieve highly unexpected process efficiencies along with extremely high product purities.

As shown in FIGS. 1–6, the paraxylene purification process of this invention generally comprises a final product separator, a final product separator feed section which may comprise a crystallization stage, and a total of at least two crystallization stages operating with different slurry outlet temperatures. The final product separator can be a system based on a wash column as described in U.S. Pat. Nos. 4,332,599; 4,491,462; and 4,475,355; a centrifuge; or a filter. Warm temperatures to the final product separator promote high product purity and high equipment capacity. In addition, there may be a third crystallization stage with or without a separation system. The paraxylene product is entirely separated from a crystal-liquid slurry by one or more final product separators. The final product separator feed section slurry being fed to the final product separator should have a relatively high temperature in the range of about −5° C. to +10° C., preferably in the range of 0° C. to +8° C. Because of thermodynamic equilibrium, the liquid phase of the slurry for this temperature range of −5° C. to +10° C. is about 61.8 to 92.1 percent paraxylene. The rest of the process is set up to economically provide this desired slurry feed to the final product separator, which in various embodiments can be systems based on a wash column, centrifuge, or filter. In a preferred embodiment, the final product separator is a packed-bed wash column system.

The process of this invention should have two or more crystallization stages. A crystallization stage in accordance with this invention can comprise one of several different designs. One useful crystallization stage design is based on the use of scraped-surface double-pipe heat exchangers with the process slurry formed inside the inner pipe and cooling provided between the pipes. This cooling can be provided by boiling refrigerant or a circulating fluid which carries heat from the scraped-surface heat exchangers to the refrigeration system. These heat exchangers can operate on a once through basis or with recirculation to increase velocities for better heat transfer to the slurry. If there is recirculation, then the main flow should go from a vessel to a pump to the exchanger crystallizers and back to the same vessel. This vessel provides cooling for the feed to the crystallizer stage, holdup for stabilizing the process, and also residence time for crystal growth. The net slurry product can be taken from the circulation either before or after the exchanger crystallizers. The net slurry product can either go to the next part of the process directly or through another vessel for additional crystal growth.

A second design for a crystallization stage is to use a vertical scraped-surface jacketed vessel. The process slurry is created inside the vessel, and the vessel jacket has either boiling refrigerant or circulating heat transfer fluid. If required for capacity, there may be multiple crystallizers in parallel.

A third design for a crystallization stage is to operate two or more vessel crystallizers in series. Each crystallizer is referred to as a step, with the warmest crystallizer called the first step. In this design, slurry from the warmest crystallizer is the crystal product of the stage. The slurry from each of the other crystallizers is fed to the next warmest. The slurry is taken off the bottom of each crystallizer. The liquid feeds to the stage are fed to the warmest crystallizer. Filtrate from each crystallizer is separated by gravity in the top section of the crystallizer. In the case of the coldest crystallizer, the filtrate is drawn off as the net filtrate from the stage. The filtrate from each of the other crystallizers in the stage is decanted off and fed to the next coldest crystallizer. In this way, the liquid streams and slurry streams between crystallizers flow countercurrently.

Still a fourth design for a crystallization stage is to use exchanger systems, as described for the first crystallization stage type described above, in series, in place of vessel-type crystallizers in the arrangement in the third design. The filtrate from each step of the stage is drawn off the top of one of the vessels in the step.

A fifth design for a crystallization stage is to use vessel-type crystallizers in series where there is no crystal/liquid separation in the crystallizers, the slurry product of the stage is from the coldest crystallizer, and the slurry from each of the warmer crystallizers flows to the next coldest crystallizer. The first (coldest) stage of the process described in U.S. Pat. No. 3,177,265 is of this type.

A sixth design for a crystallization stage is to use exchanger systems, as described for the first crystallizer stage given above, in series, in place of vessel-type crystallizers in the arrangement given in the fifth design.

The slurry feed to the final product separator comes from the final product separator feed section, which can either be a drum with pump(s) and agitator(s) or a crystallization stage. If the concentration of paraxylene in the fresh feed is equal to or less than the equilibrium concentration of paraxylene in the liquid phase of the slurry feeding the final product separator, then this section should be a drum system. If the concentration of paraxylene in the fresh feed is significantly higher than in the slurry liquid phase, then it may be advantageous to have the final product separator fed from a crystallization stage. In this latter case, the feed is at least partially fed to this stage for fractional crystallization. This crystallization stage is referred to as the "hot" crystallization stage because it operates at a higher temperature than other crystallization stage(s). The final product separator feed section is fed crystals from other parts of the process, fresh feed in some cases, and recycle filtrate from the final product separator for control of the solids concentration in the feed to the final product separator.

Upstream of the final product separator feed section is the warm crystallization stage which may be in combination with a crystal/liquid separation system, which, for example, may be based on either a centrifuge or filter. This warm stage is fed fresh feed if it is not all fed to the final product separator feed section, part of the recycle filtrate from the final product separator, and possibly crystal slurry or cake from a cold crystallization stage. The coldest process temperature in the warm crystallizer stage is typically no colder than about −20° C., and the warmest slurry temperature in this stage is no warmer than about +5° C. From this warm-stage crystallization stage or its associated separation system, the crystals are fed to the final product separator feed section, some liquid may be recycled back to the warm crystallization stage for controlling the solids concentration, and the net liquid from the stage either is the net filtrate of the process or is the feed to the cold crystallizer stage.

If there is a cold crystallization stage, it is fed directly or indirectly the net filtrate from the warm stage. It is not necessary to install this cold stage if the recovery is adequate without it. The cold stage can operate with or without a dedicated slurry separation device, such as a centrifuge or filter. With a separation device, the crystal cake is sent to the warm stage or the final product separator feed section, and part of the filtrate from the device is the net filtrate of the process. Without the separation device, the crystallization stage must have the capability to decant off the net process filtrate, and the slurry is sent to the warm crystallization stage. Appropriate heat exchangers can be added to recover cold from the product paraxylene and net filtrate, as well as to cool the fresh feed.

In a preferred embodiment of this invention, a packed-bed wash column system is used for the final separation of paraxylene crystals from the slurry. In one embodiment of the packed-bed wash column, the slurry is fed to the bottom of the column. The filtrate is removed from the bottom, while the purified crystals are transported internally to the top of the column. The crystals form a packed bed and are scraped off the top of the bed into the top head of the wash column, where they are reslurried with pure paraxylene liquid. The slurry flows from the top head, and the crystals are melted in a heat exchanger. Part of the melt is taken off as the net product, and the rest is recirculated back to the top head to reslurry the crystals and to provide liquid to reflux the wash column. The reflux is essentially all recrystallized within the wash column when the crystals are heated. Packed-bed wash columns, which are especially well suited for use in combination with the crystallization process of this invention, are described in U.S. Pat. Nos. 4,316,368; 4,332,599; 4,491,462; 4,475,355; 4,705,624; 4,787,985; and 5,062,862, which patents are incorporated herein by reference.

FIGS. 1–6, corresponding to the various examples as discussed below, illustrate several specific embodiments of this invention, each adapting and optimizing the general principles of this invention to suit particular plant conditions, feed stream purities, and other process parameters.

EXAMPLE 1

FIG. 1 is a schematic of an embodiment of the present invention in which fresh feed, typically containing between about 65 and 90 percent paraxylene, is cooled against paraxylene product from the final product separator, which in these examples is a packed-bed wash column system. The fresh feed is then combined with recycled filtrate streams from the packed-bed wash column and the warm centrifuge. The amount of filtrate recycled from the warm centrifuge is used to control the concentration of crystals in the warm crystallization stage. The combined stream is then fed with the crystals from the cold centrifuge to the warm crystallization stage.

The warm crystallization stage cools the combined stream and increases the crystal concentration. The resulting slurry is then fed to the warm centrifuge. Part of the centrifuge filtrate is recycled to the warm crystallization stage, as previously described, while the remaining filtrate becomes the feed to the cold crystallization stage. The crystals from the warm centrifuge drop into a slurry drum. In the slurry drum, the crystals from the warm centrifuge are mixed with recycled filtrate from the wash column. The amount of filtrate recycled is set to control the concentration of crystals leaving the slurry drum. To warm the crystals, a small amount of heat may be added to the slurry drum or, alternatively, heat may be added to one or more of the feed streams to the slurry drum, for example by passing the recycled filtrate through a heat exchanger.

From the slurry drum, the slurry stream is pumped to the wash column. In the wash column, the crystals are separated from the filtrate and washed of impurities. The filtrate is recycled, with a portion going to the slurry drum and the rest being sent to the warm crystallization stage. The crystals from the wash column are melted in the wash column system, heated against the feed, and pumped to storage as the purified paraxylene product.

The net filtrate from the warm centrifuge is combined with recycled filtrate from the cold centrifuge and fed to the cold crystallization stage, where cooling and crystallization occur. The slurry from the cold crystallization stage goes to the cold centrifuge. The crystals from the cold centrifuge are sent back to the warm crystallization stage. Part of the filtrate from the cold centrifuge is recycled to the cold crystallization stage for crystal concentration control. The remaining filtrate is warmed up in a heat exchanger and sent to storage.

Referring now specifically to FIG. 1, a fresh or partially purified paraxylene feed stream 101 comprising about 65 to 90 percent paraxylene, for example from an STDP process as previously described, is passed through heat exchanger 102 and then fed as stream 103 to a first (warm) crystallization stage 104 operated with an outlet temperature of about −15° C. to +5° C., depending on the feed purity. Slurry 106 from crystallizer 104 is fed to a first (warm) centrifuge 108 which separates a paraxylene crystal product stream 110 at about 98 percent purity from a mother liquor stream 112. Crystal stream 110 is fed to a slurry drum 111 operated in the range of 0° C. to +10° C., preferably about +7° C. Stream 112 is split into a recycle stream 114, which is returned to crystallizer 104, and a stream 116 which is sent to a second (cold) crystallization stage 118 operated with an outlet temperature of about −15° C. to −35° C.

Slurry 120 from crystallizer 118 is fed to a second (cold) centrifuge 122 which separates a paraxylene crystal product stream 124 from a mother liquor stream 126. A portion 128 of stream 126 is recycled to crystallizer 118, and another portion 130 is passed through a heat exchanger 132 and removed from the system as net filtrate 134. Crystal stream 124 is fed to crystallizer 104 together with feed streams 103, 114 and 154.

Slurry stream 140 from slurry drum 111 is then fed to wash column system 142 as a final product separator. Wash column system 142, which includes a melter, provides a countercurrent flow such that paraxylene crystals are "washed" with liquid paraxylene to remove crystal impurities and to attain the desired 99.9+ percent product purity. Purified paraxylene crystals are withdrawn as product stream 144 from the wash column system, passed through heat exchanger 102 to cool the feed, and the desired product is a liquid stream 146 of purified paraxylene at a temperature of about 30° C. to 35° C. Liquid stream 150 is recovered from the wash column system 142. A portion of stream 150 is recycled as stream 152 through a heat exchanger (not shown) or similar warming means to slurry drum 111, while another portion 154 of stream 150 is mixed with feedstream 103 going to crystallization stage 104.

In the FIG. 1 embodiment, multiple warm and cold stage crystallizers may be operated in parallel or in series in each crystallization stage to accommodate particular processing volumes. A key aspect of this invention is to process the paraxylene feed in such a way as to deliver relatively large and relatively warm paraxylene crystals in a slurry to the final product separator. It has been found that promoting the growth of larger crystals during the purification process both reduces material handling requirements and promotes higher product purity. With smaller crystals, the relatively larger crystal surface area makes it more difficult to separate crystals from mother liquor. Moreover, a "ripening" phenomenon has been found to lead to the growth of larger, purer crystals and melting of smaller, less pure crystals under appropriate process conditions. For relatively small temperature drops within the crystallization stages requiring multiple crystallizers because of large cooling requirements, the crystallizers may be used in parallel to reduce handling of the developing crystals and to reduce pumping requirements. For larger temperature drops, however, it is preferred to put multiple crystallizers in series at gradually decreasing temperatures to reduce temperatures shocks that could precipitate the formation of small particles rather than to promote the preferred formation of larger crystals.

For a plant producing about 35,000 kilograms per hour of 99.9+ percent pure paraxylene product from a feed containing about 82.6 percent paraxylene, the warm crystallization stage in this example could comprise vessel crystallizers operating in parallel with a slurry outlet temperature of about −1° C. The cold crystallization stage could comprise vessel crystallizers operating in series with slurry outlet temperatures in the range of −14° C. to −30° C. The flow of slurry in the cold crystallization stage is from the warmest to the coldest crystallizer. The slurry drum feeding the wash columns could operate at about +7° C. A recovery of about 90.7 percent of the paraxylene in the fresh feed is obtained with this example of the process according to the present invention.

EXAMPLE 2

Figure 4:
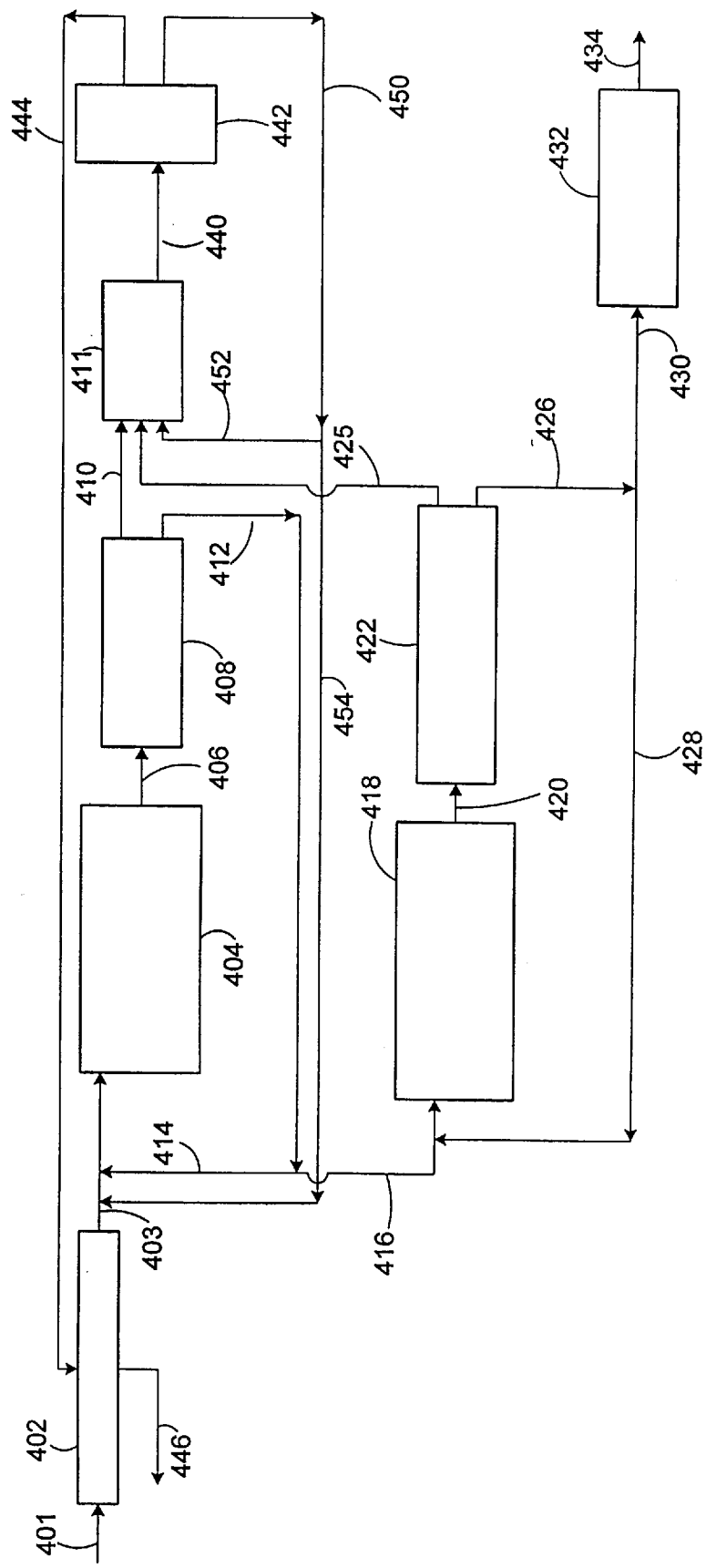
FIG. 4 is a process flow diagram illustrating an embodiment of this invention wherein purified paraxylene is produced by a two-stage process similar to that in FIG. 1 except the cold-stage crystals are fed to the slurry drum instead of the warm stage.

FIG. 4 is a schematic of an embodiment of the present invention in which the fresh feed, typically containing between about 65 and 90 percent paraxylene, is cooled against paraxylene product from the final product separator, which in this example is a packed-bed wash column system. The fresh feed is then combined with recycled filtrate streams from the wash column and the warm centrifuge. The amount of filtrate recycled from the warm centrifuge is used to control the crystal concentrations in the warm crystallization stage. The combined stream is fed to the warm crystallization stage.

Referring now specifically to FIG. 4, FIG. 4 illustrates an alternative embodiment of this invention similar to FIG. 1 in which the generally corresponding apparatus components and product flow streams bear corresponding reference numerals but utilizing a "400+" numbering series respectively in place of the "100+" numbering series utilized for FIG. 1. Thus, heat exchanger 402 corresponds to heat exchanger 102, and so forth. The principal differences between FIGS. 1 and 4 are with respect to the preferred operating temperature range of the cold-stage crystallizer and the routing of the crystals from the cold-stage centrifuge.

More particularly, cold crystallization stage 418 in FIG. 4 preferably operates at warmer temperatures than that of crystallization stage 118 in FIG. 1. The reason for this difference in the FIG. 4 embodiment relative to FIG. 1 is that the crystals withdrawn from cold-stage centrifuge 422 as product stream 425 are directed straight to slurry drum 411 in contrast to comparable stream 124 in FIG. 1 which is directed back to the warm crystallization stage 104. The ability to successfully utilize this aspect of the FIG. 4 embodiment depends on whether the cold-stage crystals in stream 425 are sufficiently large that they do not require the additional "ripening" time and two-step warming that benefit the crystals in stream 124. Because the FIG. 4 embodiment preferably operates at a somewhat warmer cold-stage crystallization temperature and bypasses a second, relatively expensive centrifuge operation for the partially purified cold-stage crystals, this embodiment realizes additional process efficiencies relative to FIG. 1 with a possible tradeoff of lower recovery.

In this embodiment of the invention, the warm crystallization stage cools the combined stream and forms crystals. The resulting slurry 406 is then fed to the warm centrifuge 408. Part 414 of the centrifuge filtrate is recycled to the warm crystallization stage, as previously described, while the remaining filtrate 416 becomes the feed to the cold crystallization stage. The crystals 410 from the warm centrifuge drop into a slurry drum. In the slurry drum, the crystals from the warm centrifuge are mixed with heated recycled filtrate 452 from the wash column. The amount of filtrate recycled is set to control the concentration of crystals leaving the slurry drum.

From the slurry drum, the slurry stream 440 is pumped to the wash column. In the wash column, the crystals are separated from the filtrate and washed of impurities. The filtrate 450 is recycled, with a portion 452 passing through a heat exchanger (not shown) and then going to the slurry drum and the rest 454 being sent to the warm crystallization stage. The crystals from the wash column are melted in the melter that is part of the wash column system, heated against the feed, and pumped to storage as the purified paraxylene product 446.

The net filtrate 416 from the warm centrifuge is combined with recycled filtrate 428 from the cold centrifuge and fed to the cold crystallization stage, where cooling and crystallization occur. The slurry 420 from the cold crystallization stage goes to the cold centrifuge 422. Part 428 of the filtrate from the cold centrifuge is recycled to the cold crystallization stage for crystal concentration control. The remaining filtrate is warmed up in a heat exchanger and sent to storage as a net product 434.

EXAMPLE 3

Figure 2:
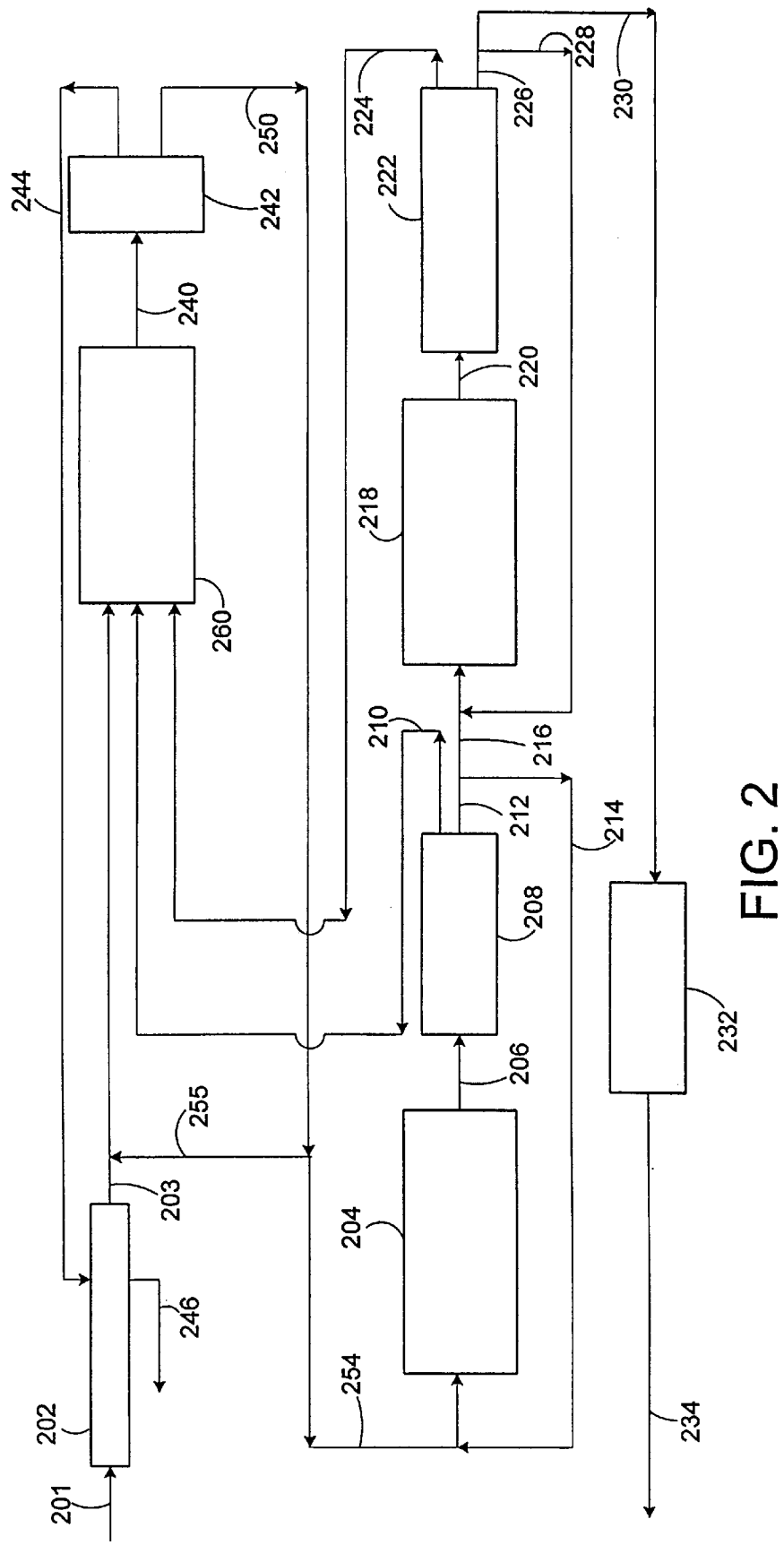
FIG. 2 is a process flow diagram illustrating an embodiment of this invention wherein purified paraxylene is produced by a three-stage process where the final product separator feed section comprises a hot crystallization stage. The separated crystals from the other two stages are fed to the hot stage.

FIG. 2 is a schematic of an embodiment of the present-invention in which the fresh feed to the crystallization unit typically contains between about 70 to 95 percent paraxylene. The fresh feed is cooled against the paraxylene product from the final product separator which, in this case, is a packed-bed wash column system, and is fed to the "hot" crystallization stage. The fresh feed is then mixed with the crystals from the warm and cold centrifuges and recycled filtrate from the wash column and fed to the hot crystallization stage. The amount of filtrate is set to control the crystal concentration in the hot crystallization stage.

Referring now specifically to FIG. 2, FIG. 2 illustrates an alternative embodiment of this invention somewhat similar to FIG. 4 in which the generally corresponding apparatus components and product flow streams bear corresponding reference numerals but utilizing a "200+" numbering series respectively in place of the "400+" series used for FIG. 4.

Similar to the FIG. 4 embodiment, in FIG. 2 cold-stage crystal cake coming from cold-stage centrifuge 222 are not processed in an expensive second centrifuge operation, as in FIG. 1. In place of slurry drum 411, however, the FIG. 2 embodiment utilizes a third (hot) crystallization stage 260 operated with an outlet temperature in the range of −5° C. to +10° C., preferably above 0° C. In this embodiment, crystals from the warm-stage centrifuge 208, represented by flow stream 210, as well as crystals from the cold-stage centrifuge 222, represented by flow stream 224, are directed to the hot crystallization stage 260 along with incoming feed stream 203. Slurry 240 from crystallizer 260, typically comprising about 35 percent solids, goes to wash column system 242. A portion 255 of liquid stream 250 from the bottom of the wash column is recycled into feed stream 203, while another portion 254 is sent to warm crystallizer 204.

The embodiment of FIG. 2 is particularly efficient for relatively large scale plants processing sufficient amounts of relatively pure paraxylene feed to justify the higher fixed costs of three crystallization stages, each of which may comprise multiple crystallizers. Relatively pure paraxylene refers here to paraxylene of at least about 70 percent purity because at purities below 70 percent, low percentages of paraxylene crystallize at −5° C. Thus, at purities below 70 percent, the third (hot) crystallization stage 260 operating at about −5° C. would not produce many crystals. With crystallization being carried out at three temperatures, temperature changes for the developing crystals can be carried out more gradually thereby facilitating the growth of larger crystals at warmer temperatures and thereby also minimizing refrigeration costs.

The crystal slurry stream 240 from the hot crystallization stage is sent directly to the wash column for purification. In the wash column, the filtrate is separated from the crystals. The filtrate is recycled, with a portion going to the hot crystallization stage and the rest being sent to the warm crystallization stage. The crystals from the wash column are melted in the wash column system, heated against the fresh feed, and pumped to storage as the paraxylene product 246.

The filtrate 254 from the wash column is mixed with recycled filtrate 214 from the warm centrifuge and fed to the warm crystallization stage 204. The slurry produced in the warm crystallization stage is fed to the warm centrifuge 208. The crystals 210 from the warm centrifuge are sent to the hot crystallization stage. Part 214 of the warm stage filtrate is recycled to the warm crystallization stage for crystal concentration control, while the remaining filtrate 216 is fed to the cold crystallization stage.

Part 216 of the filtrate from the warm centrifuge is mixed with a portion 228 of the filtrate from the cold centrifuge and fed to the cold crystallization stage 218. The crystal slurry stream 220 from the cold crystallization stage goes to the cold centrifuge 222. The crystals 224 from the cold centrifuge are sent to the hot crystallization stage. The nonrecycled part 230 of the filtrate is warmed up in a heat exchanger 232 and sent to storage as a net product 234.

For a paraxylene production of about 50,000 kilograms per hour from a fresh feed containing about 90 percent paraxylene, the hot crystallization stage could comprise exchanger crystallizers operating with an outlet temperature of about +7° C. The warm crystallization stage could comprise exchanger crystallizers operating with outlet temperatures of about −3° C., and the cold crystallization stage could comprise an exchanger crystallizer operating with outlet temperatures of about −20° C. A recovery of about 92.5 percent of the paraxylene in the fresh feed is obtained with this process.

EXAMPLE 4

Figure 6:
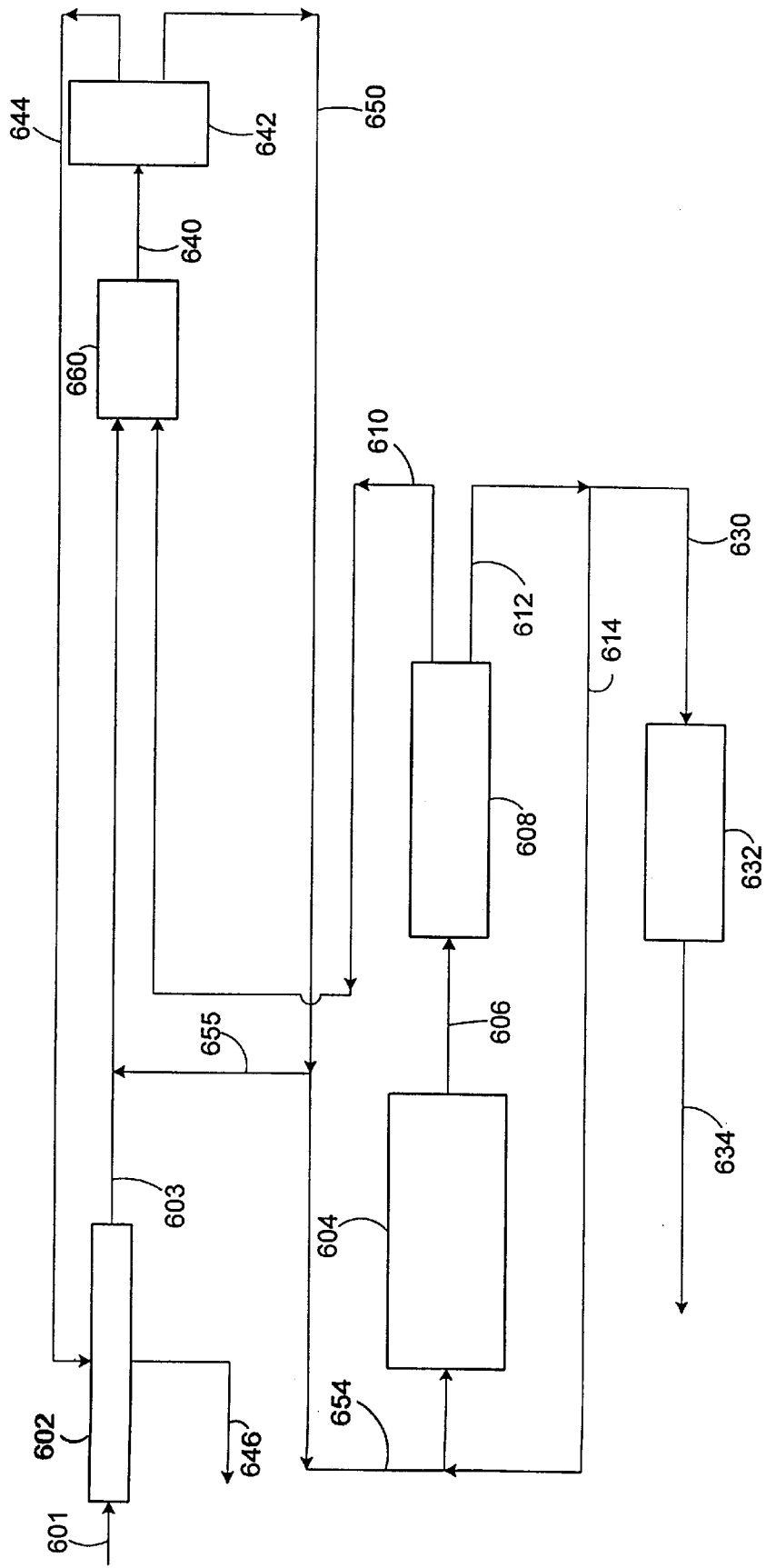
FIG. 6 is a process flow diagram illustrating an embodiment of this invention wherein purified paraxylene is produced by a two-stage process similar to that in FIG. 2 except the cold crystallization stage and cold-stage separator have been deleted.

FIG. 6 is a schematic of an embodiment of the present invention which is the same as the embodiment in FIG. 2 except that the cold crystallization stage has been deleted. In this version of the process, the fresh feed to the crystallization unit typically contains between about 75 to 98 percent paraxylene. The fresh feed is cooled against the paraxylene product from the final product separator, which in this case is a packed-bed wash column system, and is fed to the hot crystallization stage. The fresh feed is then mixed with the crystals from the warm centrifuge and recycled filtrate from the wash column. The amount of recycled filtrate is set to control the crystal concentration in the hot crystallization stage.

Referring now specifically to FIG. 6, FIG. 6 illustrates an alternative embodiment of this invention somewhat comparable to FIG. 2 in which the generally corresponding apparatus components and product flow streams bear corresponding reference numerals but utilizing a "600+" numbering series respectively in place of the "200+" series used for FIG. 2. The principal difference between the FIG. 6 and FIG. 2 embodiments is that FIG. 6 is optimized for higher purity feed streams. Because of the higher purity of the starting feed in this embodiment, it is possible to dispense with the cold-stage crystallization and centrifuge steps. Thus, all of the mother liquor 612 from warm centrifuge 608 is either recycled as stream 614 or sent as stream 630 to heat exchanger 632 for processing as net filtrate 634.

The crystal slurry stream 640 from the hot crystallization stage 660 is sent directly to the wash column system 642 for purification. In the wash column, the filtrate is separated from the crystals. The filtrate is recycled, with a portion 655 going to the hot crystallization stage 660 and the rest 654 being sent to the warm crystallization stage 604. The crystals from the wash column are melted in the wash column system, heated against the fresh feed, and pumped to storage as the paraxylene product 646.

Part 654 of the filtrate from the wash column is mixed with recycled filtrate 614 from the warm centrifuge 608 and fed to the warm crystallization stage 604. The slurry 606 produced in the warm crystallization stage is fed to the warm centrifuge. The crystals 610 from the warm centrifuge are sent to the hot crystallization stage. Part 614 of the warm stage filtrate is recycled to the warm crystallization stage for crystal concentration control, while the remaining filtrate 630 is the net filtrate from the unit. It is heated and then sent to storage.

For a 99.9+ percent purity paraxylene production of about 12,000 kilograms per hour from a fresh feed containing about 94 percent paraxylene, the hot and warm crystallization stages could each comprise a vessel-type crystallizer operating with an outlet temperature of about +7° C. and −3° C., respectively. The net filtrate is heated by heat exchange with the fresh feed. A recovery of about 88 percent of the paraxylene in the fresh feed is obtained with this process.

EXAMPLE 5

Figure 3:
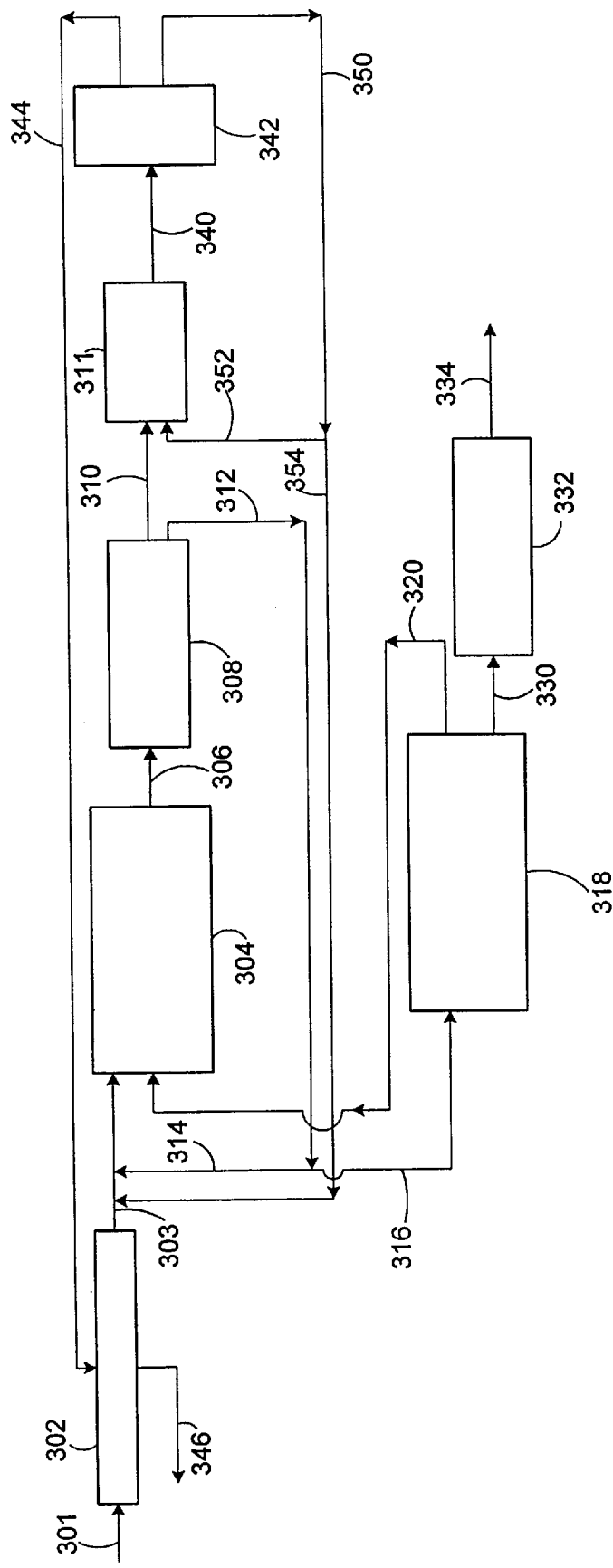
FIG. 3 is a process flow diagram illustrating an embodiment of this invention wherein purified paraxylene is produced by a two-stage process similar to that in FIG. 1 except there is no cold separator and the cold-stage crystal product is a slurry instead of a cake.

FIG. 3 is a schematic of an embodiment of the present invention in which the fresh feed, typically containing between about 65 and 90 percent paraxylene, is cooled against paraxylene product-from the final product separator, which in this example is a packed-bed wash column system. The fresh feed is then combined with recycled filtrate streams from the wash column and the warm centrifuge. The amount of filtrate recycled from the warm centrifuge is used to control the crystal concentrations in the warm crystallization stage. The combined stream is fed with crystal slurry from the cold crystallization stage.

Referring now specifically to FIG. 3, FIG. 3 illustrates an alternative embodiment of this invention similar to FIG. 1 in which the generally corresponding apparatus components and product flow streams bear corresponding reference numerals but utilizing a "300+" numbering series respectively in place of the "100+" numbering series utilized for FIG. 1. The principal difference between the FIG. 3 and FIG. 1 embodiments is that FIG. 3 is the elimination of the cold-stage centrifuge. Thus, slurry 320 from cold crystallization stage 318 is directed to warm crystallization stage 304 for further processing. The result is some relatively minor inefficiency because extra liquid that otherwise would have been removed in the cold centrifuge instead remains with the crystals and has to be moved around, and the warm crystallization stage must operate colder. However, it has been found that for some designs, the inefficiency is counterbalanced by the capital savings associated with a centrifuge operation as found in FIGS. 1 and 4.

The warm crystallization stage 304 cools its combined feeds and increases the crystal concentration. The resulting slurry 306 is then fed to the warm centrifuge 308. Part 314 of the centrifuge filtrate is recycled to the warm crystallization stage as previously mentioned, while the remaining filtrate 316 becomes the feed to the cold crystallization stage 318. The crystals 310 from the warm centrifuge 308 drop into a slurry drum 311. In this slurry drum, the crystals from the warm centrifuge are mixed with heated recycle filtrate 352, heated for example with a heat exchanger or similar means, from the wash column. The amount of filtrate recycled is set to control the concentration of crystals leaving the slurry drum.

From the slurry drum, the slurry stream 340 is pumped to the wash column. In the wash column, the filtrate is removed from the bottom, while the crystals are separated from the filtrate and washed of impurities. The filtrate is recycled, with a portion 352 going to the slurry drum and the rest 354 being sent to the warm crystallization stage 304. The crystals from the wash column are melted in the wash column system and drawn off to form the paraxylene product 344. The product stream from the wash column system is heated against the fresh feed and pumped to storage as product stream 346.

Part 316 of the filtrate from the warm centrifuge is fed to the cold crystallization stage 318, where cooling and crystallization occur. The slurry 320 from the cold crystallization stage is sent to the warm crystallization stage. The net filtrate 330 is decanted off a vessel in the cold crystallization stage, warmed up in a heat exchanger, and sent to storage.

For a plant producing about 6,000 kilograms per hour of 99.9+ percent paraxylene product from a fresh feed containing about 76 percent paraxylene, the warm crystallization stage could comprise one vessel crystallizer with a slurry outlet temperature of −13° C. The cold crystallization stage could comprise one vessel crystallizer operating with slurry outlet temperature of about −28° C. and a crystal concentration of about 40 percent. The slurry drum feeding the wash column could operate at about +7° C. A recovery of about 85 percent of the paraxylene in the fresh feed is obtained with this process.

In a variation of this embodiment of the invention suitable for certain process parameters, the warm-stage crystal/liquid separator 308 and slurry drum 311 may be eliminated, and slurry from warm crystallizer 304 fed directly to the final product separator 342.

EXAMPLE 6

Figure 5:
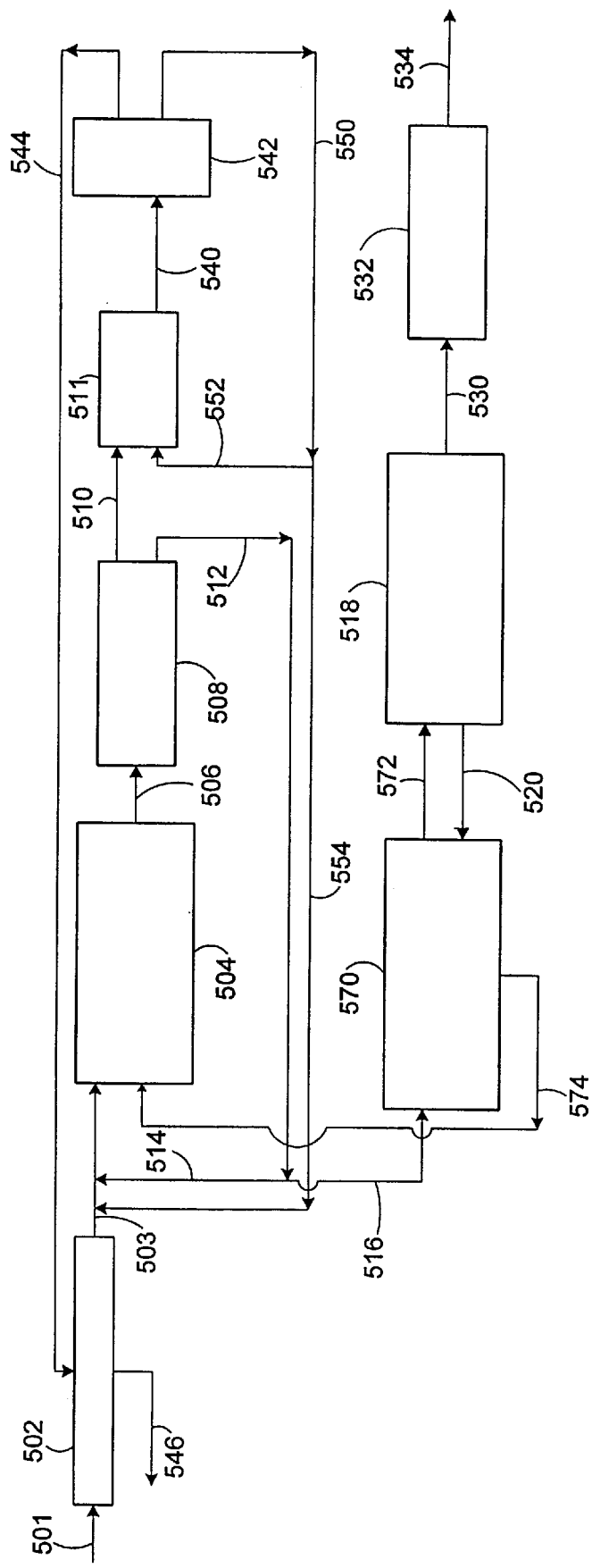
FIG. 5 is a process flow diagram illustrating an embodiment of this invention wherein purified paraxylene is produced by a two-stage process similar to that in FIG. 3 except a crystallizer drum has been added between the warm and cold stages.

FIG. 5 is a schematic of an embodiment of the present invention which is the same as the embodiment in FIG. 3 except that a crystallizer drum has been added. In this version of the process, the fresh feed, typically containing between about 65 and 90 percent paraxylene, is cooled against paraxylene product from the final product separator, which in this example is a packed-bed wash column system. The fresh feed is then combined with recycled filtrate streams from the wash column and the warm centrifuge. This combined stream is fed with crystal slurry from the cold crystallization stage by way of the crystallizer drum to the warm stage. The amount of filtrate recycled from the warm centrifuge is used to control the crystal concentrations in the warm crystallization stage.

Referring now specifically to FIG. 5, FIG. 5 illustrates an alternative embodiment of this invention similar to FIG. 3 in which the generally corresponding apparatus components and product flow streams bear corresponding reference numerals but utilizing a '500+" numbering series respectively in place of the "300+" numbering series utilized for FIG. 3. The FIG. 5 embodiment, however, provides for an additional step between the cold and warm crystallization stages to facilitate more gradual temperature increases and to spread the temperature difference between the two crystallization stages. A drum such as 570 represents lower capital and material handling costs than would another crystallizer or a centrifuge. Thus, in FIG. 5, warm centrifuge filtrate stream 516 is directed into crystallizer drum 570 which is operated at a temperature intermediate between that of the warm- and cold-stage crystallization stages. Mother liquor from drum 570 is passed as product stream 572 to cold crystallization stage 518. Slurry from crystallization stage 518 is then fed to drum 570 as product stream 520 to warm the developing crystals and to cool the liquid 516 from the warm centrifuge. The warmed slurry from drum 570 is then directed as stream 574 to the warm crystallization stage 504 for further warming and crystal growth.

The warm crystallization stage cools the feed with the recycles and increases the amount of crystals. The resulting slurry 506 is then fed to the warm centrifuge 508. Part 514 of the centrifuge filtrate is recycled to the warm crystallization stage as previously mentioned, while the remaining filtrate 516 becomes a feed to crystallizer drum 570. The crystals 510 from the warm centrifuge drop into a slurry drum 511. In this slurry drum, the crystals from the warm centrifuge are mixed with heated recycle filtrate 552, heated for example with a heat exchanger or similar means, from the wash column. The amount of filtrate recycled is set to control the concentration of crystals leaving the slurry drum.

From the slurry drum, the slurry stream 540 is pumped to the wash column. In the wash column, the filtrate is removed from the bottom, while the crystals are separated from the filtrate and washed of impurities. The filtrate is recycled, with a portion 552 going to the slurry drum and the rest 554 being sent to the warm crystallization stage 504. The crystals from the wash column are melted in the wash column system and drawn off to form the paraxylene product 544. The product stream from the wash column system is heated against the fresh feed and pumped to storage as product stream 546.

Part 516 of the filtrate from the warm centrifuge is fed to the crystallizer drum 570 along with slurry 520 from the cold crystallization stage 518. In this drum, the filtrate is cooled and the slurry is heated. Depending on the temperatures, solids concentrations, and flowrates of the two inlet streams, there may be a small amount of melting or crystal growth in this drum. Out of the bottom of the drum, slurry 574 is sent to the warm crystallization stage. The upper section of the crystallizer drum is used to separate a liquid feed 572 for the cold crystallization stage from most of the crystals.

The purpose of the crystallizer drum 570 in this embodiment is to reduce the temperature differences between the warm crystallization stage 504 and its slurry feed 574 and between the cold crystallization stage 518 and its filtrate feed 572. The addition of the drum to the process design (FIG. 3 is the same except for the addition of this drum) can also result in a higher warm crystallization stage temperature. The smaller temperature differences and higher crystallization temperature both promote the growth of larger crystals.

The clarified liquid 572 from the top of the crystallizer drum is fed to the cold crystallization stage, where cooling and crystallization occur. The slurry 520 from the cold crystallization stage is sent to the crystallizer drum. The net filtrate 530 is decanted off a vessel in the cold crystallization stage, warmed up in a heat exchanger, and sent to storage.

For a plant producing about 6,000 kilograms per hour of 99.9+ percent paraxylene product from a fresh feed containing about 79 percent paraxylene, the warm crystallization stage could consist of one vessel crystallizer with a slurry outlet temperature of about −10° C. The crystallizer drum could operate at about −15° C., and the cold crystallization stage could consist of one-vessel crystallizer operating with slurry outlet temperature of about −32° C. and a crystal concentration of about 40 percent. The slurry drum feeding the wash column could operate at about +7° C. A recovery of about 89 percent of the paraxylene in the fresh feed is obtained with this process.

In a variation of this embodiment of the invention suitable for certain process parameters, the warm-stage crystal/liquid separator 508 and slurry drum 511 may be eliminated, and slurry from warm crystallizer 504 fed directly to the final product separator 542.

In still another variation of this invention embodiment suitable for certain process parameters, the warm-stage crystal/liquid separator 508 and slurry drum 511 may be eliminated, and, in addition, the positions of warm crystallizer 504 and crystallizer drum 570 are interchanged such that feed 503 flows to crystallizer drum 570 and slurry from crystallizer drum 570 is fed directly to the final product separator 542.

It will be apparent to those skilled in the art that other changes and modifications may be made in the above-described apparatus and processes without departing from the scope of the invention herein, and it is intended that all matter contained in the above description shall be interpreted in an illustrative and not in a limiting sense. More specifically, although the various embodiments of this invention have been described with reference to the purification of paraxylene, these processes may have similarly beneficial application to other types of chemical purifications.

Having described the invention, what we claim is:

1. A crystallization process for purifying paraxylene from a feedstock consisting essentially of C8-aromatic hydrocarbons comprising the steps of:

(a) passing a feedstock containing about 65 to 90 percent paraxylene to a first crystallization stage operated with an outlet temperature of about −15° C. to +5° C. to produce a first-stage slurry which is separated into first-stage crystals and first-stage mother liquor;

(b) recycling a first portion of said first-stage mother liquor to said first crystallization stage and passing a second portion of said first-stage mother liquor to a second crystallization stage operated with an outlet temperature of about −15° C. to −35° C. to produce a second-stage slurry which is separated into second-stage crystals and second-stage mother liquor;

(c) recycling a first portion of said second-stage mother liquor to said second crystallization stage and passing said second-stage crystals substantially in crystalline form to said first crystallization stage;

(d) passing said first-stage crystals substantially in crystalline form to a slurry drum operated at a temperature of about 0° C. to +10° C. to form a third-stage slurry consisting of third-stage crystals and mother liquor;

(e) passing said third-stage slurry with said third-stage crystals substantially in crystalline form to final product separator means to produce purified paraxylene crystals having a purity of 99.5 percent or higher and separator liquid;

wherein each of steps (a) to (e) is carried out in conjunction with substantially eliminating heat input to the process thereby to realize a minimum of net melting of crystals; and, (f) separating said purified crystals from said separator liquid, recycling a first portion of said separator liquid to said first crystallization stage and recycling a second portion of said separator liquid to said slurry drum, and recovering the purified paraxylene product.

2. A crystallization process for purifying paraxylene from a feedstock consisting essentially of C8-aromatic hydrocarbons comprising the steps of:

(a) passing a feedstock containing about 65 to 90 percent paraxylene to a first crystallization stage operated with an outlet temperature of about −15° C. to +5° C. to produce a first-stage slurry which is separated into first-stage crystals and first-stage mother liquor;

(b) recycling a first portion of said first-stage mother liquor to said first crystallization stage and passing a second portion of said first-stage mother liquor to a second crystallization stage operated with an outlet temperature of about −15° C. to −35° C. to produce a second-stage slurry which is separated into second-stage crystals and second-stage mother liquor;

(c) recycling a first portion of said second-stage mother liquor to said second crystallization stage;

(d) passing said first-stage and said second-stage crystals substantially in crystalline form to a slurry drum operated at a temperature of about 0° C. to +10° C. to form a third-stage slurry consisting of third-stage crystals and mother liquor;

(e) passing said third-stage slurry with said third-stage crystals substantially in crystalline form to final product separator means to produce purified paraxylene crystals having a purity of 99.5 percent or higher and separator liquid;

wherein each of steps (a) to (e) is carried out in conjunction with substantially eliminating heat input to the process thereby to realize a minimum of net melting of crystals; and, (f) separating said purified crystals from said separator liquid, recycling a first portion of said separator liquid to said first crystallization stage and recycling a second portion of said separator liquid to said slurry drum, and recovering the purified paraxylene product.

3. A crystallization process for purifying paraxylene from a feedstock consisting essentially of C8-aromatic hydrocarbons comprising the steps of:
  (a) passing a feedstock containing about 70 to 95 percent paraxylene to a first crystallization stage operated with an outlet temperature of about −5° C. to +10° C. to produce a first-stage slurry consisting of first-stage crystals and first-stage mother liquor;
  (b) passing said first-stage slurry with said first-stage crystals substantially in crystalline form to final product separator means to produce purified paraxylene crystals having a purity of 99.5 percent or higher and separator liquid;
  (c) separating said purified crystals from said separator liquid, recycling a first portion of said separator liquid to said first crystallization stage and passing a second portion of said separator liquid to a second crystallization stage operated with an outlet temperature of about +5° C. to −15° C. to produce a second-stage slurry which is separated into second-stage crystals and second-stage mother liquor;
  (d) passing said second-stage crystals substantially in crystalline form to said first crystallization stage;
  (e) recycling a first portion of said second-stage mother liquor to said second crystallization stage and passing a second portion of said second-stage mother liquor to a third crystallization stage operated with an outlet temperature of about −10° C. to −35° C. to produce a third-stage slurry which is separated into third-stage crystals and third-stage mother liquor;
  (f) recycling a first portion of said third-stage mother liquor to said third crystallization stage, and passing said third-stage crystals substantially in crystalline form to said first crystallization stage;
  wherein each of steps (a) to (f), except for said step of separating said purified crystals from said separator liquid, is carried out in conjunction with substantially eliminating heat input to the process thereby to realize a minimum of net melting of crystals; and,
  (g) recovering the purified paraxylene product from the final product separator.

4. A crystallization process for purifying paraxylene from a feedstock consisting essentially of C8-aromatic hydrocarbons comprising the steps of:
  (a) passing a feedstock containing about 70 to 98 percent paraxylene to a first crystallization stage operated with an outlet temperature of about −5° C. to +10° C. to produce a first-stage slurry consisting of paraxylene crystals and mother liquor;
  (b) passing said first-stage slurry with said paraxylene crystals substantially in crystalline form to final product separator means to produce purified paraxylene crystals having a purity of 99.5 percent or higher and separator liquid;
  (c) separating said purified crystals from said separator liquid, recycling a first portion of said separator liquid to said first crystallization stage and passing a second portion of said separator liquid to a second crystallization stage operated with an outlet temperature of about +5° C. to −25° C. to produce a second-stage slurry which is separated into second-stage crystals and second-stage mother liquor;
  (d) passing said second-stage crystals substantially in crystalline form to said first crystallization stage;
  (e) recycling a first portion of said second-stage mother liquor to said second crystallization stage;
  wherein each of steps (a) to (e), except for said step of separating said purified crystals from said separator liquid, is carried out in conjunction with substantially eliminating heat input to the process thereby to realize a minimum of net melting of crystals; and,
  (f) recovering the purified paraxylene product from the final product separator.

5. A crystallization process for purifying paraxylene from a feedstock consisting essentially of C8-aromatic hydrocarbons comprising the steps of:
  (a) passing a feedstock containing about 65 to 90 percent paraxylene to a first crystallization stage operated with an outlet temperature of about −20° C. to 0° C. to produce a first-stage slurry which is separated into first-stage crystals and first-stage mother liquor;
  (b) recycling a first portion of said first-stage mother liquor to said first crystallization stage and passing a second portion of said first-stage mother liquor to a second crystallization stage operated so as to produce a second-stage slurry, consisting of second-stage crystals and liquor, and second-stage mother liquor at a temperature of about −15° C. to −35° C.;
  (c) passing said second-stage slurry with said second-stage crystals substantially in crystalline form to said first crystallization stage;
  (d) passing said first-stage crystals substantially in crystalline form to a slurry drum operated at a temperature of about 0° C. to +10° C. to form a third-stage slurry consisting of third-stage crystals and third-stage mother liquor;
  (e) passing said third-stage slurry with said third-stage crystals substantially in crystalline form to final product separator means to produce purified paraxylene crystals having a purity of 99.5 percent or higher and separator liquid;
  wherein each of steps (a) to (e) is carried out in conjunction with substantially eliminating heat input to the process thereby to realize a minimum of net melting of crystals; and,
  (f) separating said purified crystals from said separator liquid, recycling a first portion of said separator liquid to said first crystallization stage and recycling a second portion of said separator liquid to said slurry drum, and recovering the purified paraxylene product.

6. A crystallization process for purifying paraxylene from a feedstock consisting essentially of C8-aromatic hydrocarbons comprising the steps of:
  (a) passing a feedstock containing about 65 to 90 percent paraxylene to a first crystallization stage operated with an outlet temperature of about −15° C. to +5° C. to produce a first-stage slurry which is separated into first-stage crystals and first-stage mother liquor;
  (b) recycling a first portion of said first-stage mother liquor to said first crystallization stage and passing a second portion of said first-stage mother liquor to a crystallizer drum operated at a temperature of about 0° C. to −20° C. to produce a second-stage slurry, consisting of second-stage crystals and liquor, and second-stage mother liquor;
  (c) recycling said second-stage slurry with said second-stage crystals substantially in crystalline form to said first crystallization stage and passing said second-stage mother liquor to a second crystallization stage operated so as to produce a third-stage slurry, consisting of third-stage crystals and liquor, and third-stage mother liquor at a temperature of about −15° C. to −35° C.;

(d) recycling said third-stage slurry with said third-stage crystals substantially in crystalline form to said crystallizer drum;

(e) passing said first-stage crystals substantially in crystalline form to a slurry drum operated at a temperature of about 0° C. to +10° C. to form a fourth-stage slurry consisting of fourth-stage crystals and fourth-stage mother liquor;

(f) passing said fourth-stage slurry with said fourth-stage crystals substantially in crystalline form to final product separator means to produce purified paraxylene crystals having a purity of 99.5 percent or higher and separator liquid;

wherein each of steps (a) to (f) is carried out in conjunction with substantially eliminating heat input to the process thereby to realize a minimum of net melting of crystals; and, (g) separating said purified crystals from said separator liquid, recycling a first portion of said separator liquid to said first crystallization stage and recycling a second portion of said separator liquid to said slurry drum, and recovering the purified paraxylene product.

7. A crystallization process for purifying paraxylene from a feedstock consisting essentially of C8-aromatic hydrocarbons comprising the steps of:

(a) passing a feedstock containing about 70 to 90 percent paraxylene to a first crystallization stage operated with an outlet temperature of about −5° C. to +5°0 C. to produce a first-stage slurry consisting of first-stage crystals and first-stage mother liquor;

(b) passing said first-stage slurry with said first-stage crystals substantially in crystalline form to final product separator means to produce purified paraxylene crystals having a purity of 99.5 percent or higher and separator liquid;

(c) separating said purified crystals from said separator liquid, and recovering the purified paraxylene product;

(d) recycling a first portion of said separator liquid to said first crystallization stage and passing a second portion of said separator liquid to a second crystallization stage operated so as to produce second-stage slurry, consisting of second-stage crystals and liquor, and second-stage mother liquor at a temperature of about −10° C. to −35° C.; and, (e) passing said second-stage slurry with said second-stage crystals substantially in crystalline form to said first crystallization stage;

wherein each of steps (a), (b), (d) and (e) is carried out in con-junction with substantially eliminating heat input to the process thereby to realize a minimum of net melting of crystals.

8. A crystallization process for purifying paraxylene from a feedstock consisting essentially of C8-aromatic hydrocarbons comprising the steps of:

(a) passing a feedstock containing about 70 to 90 percent paraxylene to a first crystallization stage operated with an outlet temperature of about −5° C. to +5° C. to produce a first-stage slurry consisting of first-stage crystals and first-stage mother liquor;

(b) passing said first-stage slurry with said first-stage crystals substantially in crystalline form to final product separator means to produce purified paraxylene crystals having a purity of 99.5 percent or higher and separator liquid;

(c) separating said purified crystals from said separator liquid and recovering the purified paraxylene product;

(d) recycling a first portion of said separator liquid to said first crystallization stage and passing a second portion of said separator liquid to a crystallizer drum operated at a temperature of about 0° C. to −15° C. to produce second-stage slurry, consisting of second-stage crystals and liquor, and second-stage mother liquor;

(e) recycling said second-stage slurry with said second-stage crystals substantially in crystalline form to said first crystallization stage and passing said second-stage mother liquor to a second crystallization stage operated so as to produce third-stage slurry, consisting of third-stage crystals and liquor, and third-stage mother liquor at a temperature of about −15° C. to −35° C.; and, (f) recycling said third-stage slurry with said third-stage crystals substantially in crystalline form to said crystallizer drum;

wherein each of steps (a), (b), (d), (e) and (f) is carried out in conjunction with substantially eliminating heat input to the process thereby to realize a minimum of net melting of crystals.

9. A crystallization process for purifying paraxylene from a feedstock consisting essentially of C8-aromatic hydrocarbons comprising the steps of:

(a) passing a feedstock containing about 65 to 90 percent paraxylene with two other streams to a crystallizer drum operated at a temperature of about −5° C. to +5° C. to produce a drum slurry, consisting of drum crystals and liquor, and a drum mother liquor;

(b) passing said drum slurry with said drum crystals substantially in crystalline form to final product separator means to separate purified paraxylene crystals having a purity of 99.5 percent or higher and a separator liquid, and recovering the purified paraxylene product from the final product separator;

(c) recycling all of said separator liquid to the crystallizer drum;

(d) recycling said drum mother liquor to a first crystallization stage operated so as to produce a first-stage slurry, consisting of first-stage crystals and liquor, and a first-stage mother liquor at a temperature of about −15° C. to 0° C.;

(e) passing said first-stage slurry with said first-stage crystals substantially in crystalline form to the crystallizer drum;

(f) passing said first-stage mother liquor to a second crystallization stage operating so as to produce a second-stage slurry, consisting of second-stage crystals and liquor, and a second-stage mother liquor at a temperature of about −35° C. to −10° C.; and, (g) recycling said second stage slurry with said second-stage crystals substantially in crystalline form without significant crystal melting to the first crystallization stage;

wherein each of steps (a) to (g), except for said step of recovering the purified paraxylene product from the final product separator, is carried out in conjunction with substantially eliminating heat input to the process thereby to realize a minimum of net melting of crystals.

* * * * *

UNITED STATES PATENT AND TRADEMARK OFFICE
CERTIFICATE OF CORRECTION

PATENT NO. : 5,811,629
DATED : September 22, 1998
INVENTOR(S) : Douglas S. Hubbell et al.

It is certified that error appears in the above-identified patent and that said Letters Patent is hereby corrected as shown below:

Col. 5, line 19 - after the word "process" insert the words --wherein each process--.

Col. 21, line 28 - change the expression "+5°0C." to --+5°C.--

Col. 21, line 51, change the word "con-junction" to --conjunction--.

Signed and Sealed this

Twentieth Day of April, 1999

Attest:

Attesting Officer

Q. TODD DICKINSON

Acting Commissioner of Patents and Trademarks